(12) United States Patent
Press et al.

(10) Patent No.: US 7,109,202 B2
(45) Date of Patent: Sep. 19, 2006

(54) AMINOTHAIZOLES AND THEIR USE AS ADENOSINE RECEPTOR ANTAGONISTS

(75) Inventors: Neil J Press, Horsham (GB); Roger J Taylor, Horsham (GB)

(73) Assignee: Novartis AG, Basel (CH)

( * ) Notice: Subject to any disclaimer, the term of this patent is extended or adjusted under 35 U.S.C. 154(b) by 554 days.

(21) Appl. No.: 10/432,302

(22) PCT Filed: Nov. 19, 2001

(86) PCT No.: PCT/EP01/13378

§ 371 (c)(1),
(2), (4) Date: May 21, 2003

(87) PCT Pub. No.: WO02/42298

PCT Pub. Date: May 30, 2002

(65) Prior Publication Data
US 2004/0053982 A1 Mar. 18, 2004

(30) Foreign Application Priority Data
Nov. 21, 2000 (GB) .................................. 0028383.8

(51) Int. Cl.
A61K 31/427 (2006.01)
A61K 31/497 (2006.01)
A61K 31/4436 (2006.01)
C07D 417/14 (2006.01)
C07D 277/42 (2006.01)

(52) U.S. Cl. ................. 514/255.05; 514/342; 514/370; 544/405; 546/269.7; 546/270.7; 548/191

(58) Field of Classification Search ..................... None
See application file for complete search history.

(56) References Cited

U.S. PATENT DOCUMENTS

| | | | |
|---|---|---|---|
| 5,314,889 A | 5/1994 | Boigegrain et al. | 514/253 |
| 5,332,753 A * | 7/1994 | Haddock et al. | 514/370 |
| 5,530,000 A | 6/1996 | Sanfilippo et al. | 514/252 |
| 5,668,161 A | 9/1997 | Talley et al. | 514/365 |
| 5,854,265 A | 12/1998 | Anthony | 514/341 |
| 5,859,035 A | 1/1999 | Anthony et al. | 514/365 |
| 5,872,136 A | 2/1999 | Geeham | 4/434 |
| 5,874,452 A | 2/1999 | Anthony | 514/365 |
| 5,880,140 A | 3/1999 | Anthony | 514/333 |
| 5,883,105 A | 3/1999 | Anthony | 514/277 |
| 5,939,557 A | 8/1999 | Anthony et al. | 548/335 |
| 6,051,574 A | 4/2000 | Anthony | 514/247 |
| 6,063,930 A | 5/2000 | Dinsmore et al. | 546/337 |
| 6,069,162 A | 5/2000 | Itoh et al. | 514/397 |
| 6,080,870 A | 6/2000 | Anthony et al. | 548/324.1 |
| 6,436,966 B1 | 8/2002 | Ohkawa et al. | 514/340 |

FOREIGN PATENT DOCUMENTS

| | | |
|---|---|---|
| JP | 4-118648 | 4/1992 |
| JP | 7-128824 | 5/1995 |
| JP | 2000-302680 | 10/2000 |
| WO | 99/64418 | 12/1999 |
| WO | 00/34255 | 6/2000 |
| WO | 00/66124 | 11/2000 |
| WO | 01/62247 | 8/2001 |
| WO | 01/64674 | 9/2001 |

OTHER PUBLICATIONS

Haddock et al., STN International, HCAPLUS Database, Columbus, OH, Accession No.: 1991:228903, Reg. No. 133767-42-7 (2006).*
Schuetze et al., "Thiazolylpyridinium Salts", Chemical Abstracts No. 152043u, vol. 77, p. 410 (1972).

* cited by examiner

Primary Examiner—Golam M. M. Shameem
Assistant Examiner—Andrew B. Freistein
(74) Attorney, Agent, or Firm—Gregory C. Houghton

(57) ABSTRACT

Compounds of formula (I) in free or salt form, where A is a $C_6$–$C_{15}$ monovalent aromatic group. $R^1$ is hydrogen, phenyl optionally substituted by one or more substituents selected from halogen, cyano, hydroxy, $C_1$–$C_8$-alkyl, $C_1$–$C_8$-haloalkyl, $C_1$–$C_8$-alkoxy, $C_1$–$C_8$-alkoxy-$C_1$–$C_8$-alkyl or acyloxy, or a 5- or 6-membered monovalent heterocyclic group, $R^2$ is hydrogen, $C_1$–$C_8$-alkyl, acyl or $CON(R^3)R^4$, provided that $R^2$ is $C_1$–$C_8$-alkyl, acyl or $CON(R^3)R^4$ when $R^1$ is hydrogen, $R^3$ and $R^4$ are each independently hydrogen, or $C_1$–$C_8$-alkyl, together with the nitrogen atom to which they are attached denote a 5- or 6-membered heterocyclic group, and $Z^1$, $Z^2$, $Z^3$ and $Z^4$ are each independently N or $CR^5$, at least one of them being $CR^5$, and $R^5$ is hydrogen, $C_1$–$C_8$-alkyl or $C_1$–$C_8$-alkoxy. The compounds are useful as adenosine receptor antagonists, particularly in the treatment of inflammatory or obstrucive airways diseases (I)

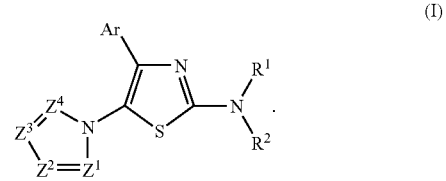

11 Claims, No Drawings

AMINOTHAIZOLES AND THEIR USE AS ADENOSINE RECEPTOR ANTAGONISTS

This invention relates to organic compounds, their preparation and their use as pharmaceuticals.

In one aspect, the present invention provides compounds of formula

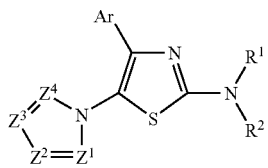

I in free or salt form, where
Ar is a $C_6$–$C_{15}$ monovalent aromatic group,
$R^1$ is hydrogen, phenyl optionally substituted by one or more substituents selected from halogen, cyano, hydroxy, $C_1$–$C_8$-alkyl, $C_1$–$C_8$-haloalkyl, $C_1$–$C_8$-alkoxy, $C_1$–$C_8$-alkoxy-$C_1$–$C_8$-alkyl or acyloxy, or a 5- or 6-membered monovalent heterocyclic group
$R^2$ is hydrogen, $C_1$–$C_8$-alkyl, acyl or —CON($R^3$)$R^4$, provided that $R^2$ is $C_1$–$C_8$-alkyl, acyl or —CON($R^3$)$R^4$ when $R^1$ is hydrogen,
$R^3$ and $R^4$ are each independently hydrogen or $C_1$–$C_8$-alkyl, or together with the nitrogen atom to which they are attached denote a 5- or 6-membered heterocyclic group,
$Z^1$, $Z^2$, $Z^3$ and $Z^4$ are each independently N or $CR^5$, at least one of them being $CR^5$, and
$R^5$ is hydrogen, $C_1$–$C_8$-alkyl or $C_1$–$C_8$-alkoxy.

Terms used in the specification have the following meanings:

"$C_1$–$C_8$-alkyl" as used herein denotes straight chain or branched $C_1$–$C_8$-alkyl, which may be, for example, methyl, ethyl, n-propyl, isopropyl, n-butyl, isobutyl, sec-butyl, tert-butyl, straight or branched pentyl, straight or branched hexyl, straight or branched heptyl, or straight or branched octyl. Preferably, $C_1$–$C_8$-alkyl is $C_1$–$C_4$-alkyl.

"$C_1$–$C_8$-alkoxy" as used herein denotes straight chain or branched $C_1$–$C_8$-alkoxy which may be, for example, methoxy, ethoxy, n-propoxy, isopropoxy, n-butoxy, isobutoxy, sec-butoxy, tert-butoxy, straight or branched pentoxy, straight or branched hexyloxy, straight or branched heptyloxy, or straight or branched octyloxy. Preferably, $C_1$–$C_8$-alkoxy is $C_1$–$C_4$-alkoxy.

"$C_1$–$C_8$-haloalkyl" as used herein denotes $C_1$–$C_8$-alkyl as hereinbefore defined substituted by one or more halogen atoms, preferably one, two or three halogen atoms, preferably fluorine or chlorine atoms. Preferably $C_1$–$C_8$-haloalkyl is $C_1$–$C_4$-alkyl substituted by one, two or three fluorine or chlorine atoms.

"$C_1$–$C_8$-alkoxy-$C_1$–$C_8$-alkyl" as used herein denotes $C_1$–$C_8$-alkyl as hereinbefore defined substituted by $C_1$–$C_8$-alkoxy as hereinbefore defined.

"$C_1$–$C_8$-alkoxy-$C_1$–$C_8$-alkoxy" as used herein denotes $C_1$–$C_8$-alkoxy as hereinbefore defined substituted by $C_1$–$C_8$-alkoxy as hereinbefore defined. "$C_1$–$C_8$-alkylcarbonyl", "$C_1$–$C_8$-haloalkylcarbonyl" and "$C_1$–$C_8$-alkoxycarbonyl" as used herein denote $C_1$–$C_8$-alkyl, $C_1$–$C_8$-haloalkyl or $C_1$–$C_8$-alkoxy respectively as hereinbefore defined attached by a carbon atom to a carbonyl group.

"Acyl" as used herein denotes alkylcarbonyl, for example $C_1$–$C_8$-alkylcarbonyl where $C_1$–$C_8$-alkyl may be one of the $C_1$–$C_8$-alkyl groups hereinbefore mentioned, optionally substituted by one or more halogen atoms; cycloalkylcarbonyl, for example $C_3$–$C_8$-cycloalkylcarbonyl where $C_3$–$C_8$-cycloalkyl may be, for example, cyclopropyl, cyclobutyl, cyclopentyl, cyclohexyl, cycloheptyl or cyclooctyl; 5- or 6-membered heterocyclylcarbonyl having one or more, preferably one or two, hetero atoms selected from nitrogen, oxygen and sulfur in the ring, such as furylcarbonyl, methylthienylcarbonyl or pyridylcarbonyl; arylcarbonyl, for example $C_6$–$C_{10}$-arylcarbonyl such as benzoyl; or aralkylcarbonyl, for example $C_6$ to $C_{10}$-aryl-$C_1$–$C_4$-alkylcarbonyl such as benzylcarbonyl or phenylethylcarbonyl.

"Acyloxy" as used herein denotes alkylcarbonyloxy, for example $C_1$–$C_8$-alkylcarbonyloxy where $C_1$–$C_8$-alkyl may be one of the $C_1$–$C_8$-alkyl groups hereinbefore mentioned, optionally substituted by one or more halogen atoms; cycloalkylcarbonyloxy, for example $C_3$–$C_8$-cycloalkylcarbonyloxy where $C_3$–$C_8$-cycloalkyl may be, for example, cyclopropyl, cyclobutyl, cyclopentyl, cyclohexyl, cycloheptyl or cyclooctyl; 5- or 6-membered heterocyclylcarbonyloxy having one or two hetero atoms selected from nitrogen, oxygen and sulfur in the ring, such as furylcarbonyloxy or pyridylcarbonyloxy; arylcarbonyloxy, for example $C_6$–$C_{10}$-arylcarbonyloxy such as benzoyloxy; or aralkylcarbonyloxy, for example $C_6$ to $C_{10}$-aryl-$C_1$–$C_4$-alkylcarbonyloxy such as benzylcarbonyloxy or phenylethylcarbonyloxy. Preferably acyloxy is $C_1$–$C_4$-alkylcarbonyloxy.

"Halogen" as used herein may be fluorine, chlorine, bromine or iodine; preferably it is fluorine or chlorine.

Ar may be, for example, phenyl optionally substituted by one or more substituents, for example, one, two or three substituents selected from halogen, cyano, $C_1$–$C_8$-alkyl or $C_1$–$C_8$-haloalkyl, or Ar may be naphthyl. Ar is preferably phenyl optionally substituted by halogen, cyano or $C_1$–$C_8$-alkyl, preferably meta or para to the indicated thiazole ring.

$R^1$ may be, for example, hydrogen, phenyl optionally substituted by halogen, cyano, hydroxy, $C_1$–$C_8$-alkyl, $C_1$–$C_8$-haloalkyl, $C_1$–$C_8$-alkoxy, $C_1$–$C_8$-alkoxy-$C_1$–$C_8$-alkyl, carboxy, $C_1$–$C_8$-alkoxycarbonyl or $C_1$–$C_8$-alkylcarbonyloxy, or a monovalent 5- or 6-membered heterocyclic group having one, two or three ring hetero atoms selected from nitrogen, oxygen and sulfur, such as pyrrolyl, triazolyl, pyridyl, oxopyridyl, piperidyl, pyridazinyl, pyrimidinyl, pyrazinyi, pyrazoiyl, pyrazoilnyi, piperazinyi, morpholinyi, turyl, pyranyl, thienyl or thiazolyl, optionally substituted by one or more substituents selected from $C_1$–$C_8$-alkyl, hydroxy, $C_1$–$C_8$-alkoxy or $C_1$–$C_8$-alkoxy-$C_1$–$C_8$-alkoxy. Preferably $R^1$ is hydrogen, phenyl optionally substituted by cyano or $C_1$–$C_4$-alkoxy, or a monovalent 6-membered N-heterocyclic group, preferably a heteroaromatic group, especially pyridyl, $C_1$–$C_4$-alkylpyridyl, di($C_1$–$C_4$-alkyl)pyridyl, $C_1$–$C_4$-alkoxypyridyl, pyrazinyl, $C_1$–$C_4$-alkylpyrazinyl, $C_1$–$C_4$-alkoxypyrazinyl or $C_1$–$C_4$-alkoxy-$C_1$–$C_4$-alkoxypyrazinyl.

$R^2$ may be, for example, hydrogen, $C_1$–$C_8$-alkyl, formyl, $C_1$–$C_8$-alkylcarbonyl, $C_1$–$C_8$-haloalkylcarbonyl, $C_3$–$C_8$-cycloalkylcarbonyl, phenylcarbonyl in which the phenyl moiety is optionally substituted by halogen, cyano, hydroxy, $C_1$–$C_8$-alkyl or $C_1$–$C_8$-alkoxy, heterocyclylcarbonyl in which the heterocyclyl group is 5- or 6-membered and has one or more, preferably one or two, ring hetero atoms selected from nitrogen, oxygen and sulfur, or a group —CON($R^3$)$R^4$. Preferably $R^2$ is hydrogen, $C_1$–$C_4$-alkylcarbonyl, $C_3$–$C_6$-cycloalkylcarbonyl, phenylcarbonyl where the phenyl group is optionally substituted by $C_1$–$C_8$-alkoxy, or heterocyclylcarbonyl in which the heterocyclyl group is 5- or 6-membered and has a ring hetero atom selected from nitrogen, oxygen and sulfur, such as furylcarbonyl, tetrahydrofirylcarbonyl, $C^1$–$C_4$-alkylfurylcarbonyl, thienylcarbonyl, $C_1$–$C_4$-alkyl-thienylcarbonyl, N—($C_1$–$C_4$-alkyl)pyrrolylcarbonyl and pyridylcarbonyl.

Where present, $R^3$ and $R^4$ may each independently be, for example, hydrogen or $C_1$–$C_4$-alkyl, or together with the nitrogen atom to which the are attached may denote a 5-membered heterocyclyl group such as pyrrolyl or pyrrolidinyl or a 6-membered heterocyclyl group such as pyridyl, piperidyl, piperazinyl or morpholinyl. Preferably $R^3$ and $R^4$, where present, are each $C_1$–$C_8$-alkyl, especially methyl, or together with the nitrogen atom to which they are attached denote a 6-membered heterocyclyl group, especially pyridyl.

When two or more of $Z^1$, $Z^2$, $Z^3$ and $Z^4$ denote $CR^5$, the $CR^5$ groups may be the same or different. Preferably $R^5$ is hydrogen or $C_1$–$C_4$-alkyl. Preferably $Z^1$ and $Z^3$ each denote N and $Z^2$ and $Z^4$ each independently denote $CR^5$, or $Z^2$ denotes N and $Z^1$, $Z^3$ and $Z^4$ each independently denote $CR^5$ where $R^5$ is hydrogen or $C_1$–$C_4$-alkyl. In especially preferred embodiments, $Z^1$ and $Z^3$ each denote N and $Z^2$ and $Z^4$ each denote CH, or $Z^1$ denotes $CR^5$ where $R^5$ is hydrogen or $C_1$–$C_4$-alkyl, $Z^2$ denotes N and $Z^3$ and $Z^4$ each denote CH.

Preferred compounds of formula I in free or salt form are those where

Ar is phenyl optionally substituted by halogen or cyano,
$R^1$ is hydrogen, phenyl optionally substituted by cyano or $C_1$–$C_4$-alkoxy, or a monovalent 6-membered N-heterocyclic group,
$R^2$ is hydrogen, $C_1$–$C_4$-alkylcarbonyl, $C_3$–$C_6$-cycloalkylcarbonyl, phenylcarbonyl where the phenyl group is optionally substituted by $C_1$–$C_4$-alkoxy, or heterocyclylcarbonyl where the heterocyclyl group is 5- or 6-membered and has one or two ring hetero atoms selected from nitrogen, oxygen and sulfur, and either $Z^1$ and $Z^3$ each denote N and $Z^2$ and $Z^4$ each denote CH, or $Z^1$ denotes $CR^5$ where $R^5$ is hydrogen or $C_1$–$C_4$-alkyl, $Z_2$ denotes N and $Z^3$ and $Z^4$ each denote CH.

Further preferred compounds of formula I in free or salt form are those where
Ar is phenyl substituted by halogen or cyano meta or para to the indicated thiazole ring,
$R^1$ is a monovalent 6-membered N-heterocyclic group,
$R^2$ is hydrogen and either $Z^1$ and $Z^3$ each denote N and $Z^2$ and $Z^4$ each denote CH, or $Z^1$ denotes $CR^5$ where $R^5$ is hydrogen or $C_1$–$C_4$-alkyl, $Z_2$ denotes N and $Z^3$ and $Z^4$ each denote CH.

Other further preferred compounds of formula I in free or salt form are those where
Ar is phenyl substituted by halogen or cyano meta or para to the indicated thiazole ring,
$R^1$ is hydrogen,
$R^2$ is phenylcarbonyl where phenyl is optionally substituted by $C_1$–$C_4$-alkoxy, or heterocyclylcarbonyl where the heterocyclyl group is 5- or 6-membered and has a ring hetero atom selected from oxygen and sulfur, and either $Z^1$ and $Z^3$ each denote N and $Z^2$ and $Z^4$ each denote CH, or $Z^1$ denotes $CR^5$ where $R^5$ is hydrogen or $C_1$–$C_4$- alkyl, $Z_2$ denotes N and $Z^3$ and $Z^4$ each denote CH.

Especially preferred specific compounds of formula I are those described hereinafter in the Examples.

The compounds represented by formula I are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid or hydroiodic acid, nitric acid, sulfuric acid, phosphoric acid; and organic acids, for example aliphatic monocarboxylic acids such as formic acid, acetic acid, trifluoroacetic acid, propionc acid and butyric acid, aliphatic hydroxy acids such as iactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid. These salts may be prepared from compounds of formula I by known salt-forming procedures.

Compounds of formula I which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of formula I by known salt-forming procedures.

The invention provides, in another aspect, a method of preparing a compound of formula I in free or salt form which comprises (i) (A) for the preparation of compounds of formula I where $R^1$ is optionally substituted phenyl or a 5- or 6-membered heterocyclic group, reacting a compound of formula

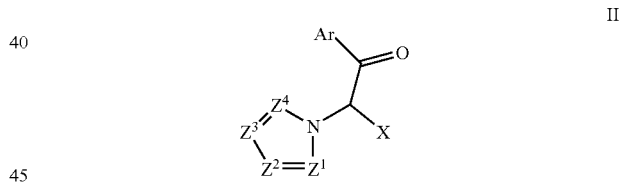

II in the form of a salt, e.g. a hydrohalide salt thereof, where Ar, $Z^1$, $Z^2$, $Z^3$ and $Z^4$ are as hereinbefore defined and X is halogen, preferably bromine or iodine, with a compound of formula

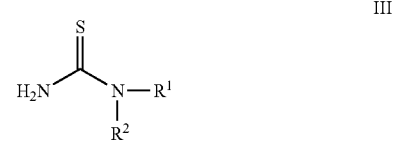

III where $R^1$ is phenyl optionally substituted by one or more substituents selected from halogen, cyano, hydroxy, $C_1$–$C_8$-alkyl, $C_1$–$C_8$-haloalkyl, $C_1$–$C_8$-alkoxy, $C_1$–$C_8$-alkoxy-$C_1$–$C_8$-alkyl and acyloxy or $R^2$ is a 5- or 6-membered monovalent heterocyclic group, and $R^2$ is H or $C_1$–$C_8$-alkyl or (B) for the preparation of compounds of Formula I where $R^1$ is optionally substituted phenyl or a 5- or 6-membered heterocyclic group, reacting a compound of formula

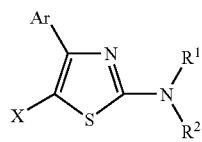

IV where Ar, $R^1$, $R^2$ and X are as hereinbefore defined, with a compound of formula

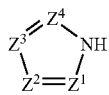

V where $Z^1$, $Z^2$, $Z^3$ and $Z^4$ are as hereinbefore defined or (C) for the preparation of compounds of formula I where $R^2$ is acyl or —$CON(R^3)R^4$, reacting a compound of formula

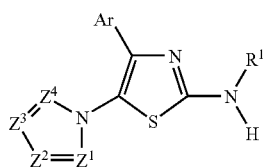

VI where Ar, $R^1$, $Z^1$, $Z^2$, $Z^3$ and $Z^4$ are as hereinbefore defined with, respectively, an acylating derivative of a carboxylic acid, for example the anhydride or acid chloride thereof, or with a compound of formula Cl—$CON(R^3)R^4$) where $R^3$ and $R^4$ are as hereinbefore defined, and (ii) recovering the resultant compound of formula I in free or salt form.

Process variant (A) may be carried out in an organic solvent, for example an alcohol such as ethanol, or a tertiary base such as pyridine. Suitable reaction temperatures are elevated temperatures, for example from 50° C. to reflux temperature of the solvent.

Process variant (B) may be carried out using known procedures, for example by heating the reactants, optionally in an inert solvent. Suitable reaction temperatures are, for example, from 80 to 160° C.

Process variant (C) may be carried out using known procedures for reaction of amines with acylating agents.

Compounds of formula II may be prepared by reacting a compound of formula

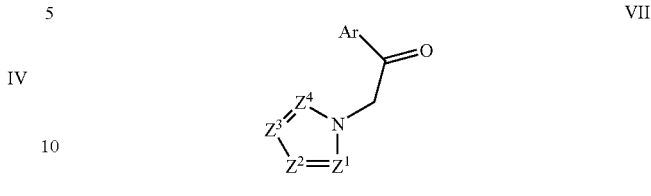

VII where Ar, $Z^1$, $Z^2$, $Z^3$ and $Z^4$ are as hereinbefore defined, with halogen $X_2$, preferably bromine. This halogenation may be effected using known procedures for alpha halogenation of ketones or analogously, for example as hereinafter described in the Examples. This reaction may be carried out in situ in the presence of the compound of formula III with which the compound of formula II is to be reacted to form a compound of formula I.

Compounds of formula III are thioureas which are either known or may be obtained by known procedures. For example they may be prepared by reaction of a compound of formula

VIII where $R^1$ and $R^2$ are as hereinbefore defined, with benzoyl isothiocyanate and hydrolysing the resulting product, for example with aqueous NaOH, to replace the benzoyl group by halogen. The reaction with benzoyl isothiocyanate may be carried out in an organic solvent, for example an alcohol such as ethanol. Suitable reaction temperatures are from room temperature to reflux temperature of the solvent, conveniently 35–45° C. The hydrolysis may be effected at elevated temperature, for example 70° C. to reflux temperature, conveniently at reflux temperature.

Compounds of formula IV may be prepared by reacting a compound of formula

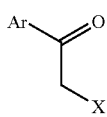

IX where Ar and X are as hereinbefore defined with a compound of formula III, for example using known procedures such as those hereinbefore described for reactions of compounds of formulae II and III, and brominating the resulting aminothiazole, for example using known procedures or variants thereof, e.g. as hereinafter described in the Examples.

Compounds of formula V are known compounds which are commercially available or may be prepared by known procedures. Compounds of formula VI may be prepared by process variant (A) or (B) as described above. Compounds of formula VII may be prepared by reaction of a compound or formula IX with the sodium derivative of a compound of formula V, e.g. using a known procedure such as described hereinafter in the Examples. Compounds of fomulae VIII and IX are known or may be obtained by known procedures such as described hereinafter in the Examples.

Compounds of formula I and their pharmaceutically acceptable salts are useful as pharmaceuticals. In particular, they exhibit inhibition of adenosine A2b receptor activation, i.e. they act as A2b receptor antagonists. Moreover, in general they selectively inhibit activation of A2b receptor over the adenosine A1 and A2a receptors. Their inhibitory properties may be demonstrated in the following test procedures:

Adenosine A2b Receptor Reporter Gene Assay a) Culturing of Chinese Hamster Ovary (CHO) A2b Cell Line CHO cells transfected with a Luciferase-expressing reporter plasmid (pCRE-LUCI) and with a plasmid carrying the human adenosine A2b receptor structural gene (pA2bRCV) are routinely cultured in Dulbecco's Modified Eagle Medium (DMEM)—supplemented with 10% v/v fetal calf serum (FCS), 2 mM L-glutamine, 0.4 mg/ml L-proline, 1 nM sodium selenite, 0.5 mg/ml Hygromycin B and 1 mg/ml Geneticin—at 37° C., 5% $CO_2$ and 100% humidity. The cells are left to grow to confluence for 4–5 days. The cells obtained are passaged using trypsin/EDTA and split at a ratio of 1 in 5.

b) Preparation of Cells for Assay

Prior to the assay, the CHO-A2b cells are plated onto white 96-well View Plate tissue culture plates (Packard) at a density of 50,000 cells per well in 50 W of DMEM, and the plates are incubated at 37° C., 5% $CO_2$ and 100% humidity.

c) Preparation of Reference and Test Compounds 10 mM solutions of the reference compound, Xanthine Amine Cogener (XAC), and the test compound in dimethyl sulfoxide (DMSO) are prepared. The solutions are further diluted with DMSO to 100 μM, then diluted to 10 μM, and finally to 250 nM or 2.5 μM with Assay Buffer (DMEM Phenol Red-free tissue culture media supplemented with 10 μM Rolipram and 10 U/ml adenosine deaminase (ADA). The resulting solutions (40 μl) are added to the cells in the appropriate wells, the final concentration per well being 100 nM or 1 μM, and the plates are incubated at 37° C., 5% $CO_2$ and 100% humidity.

d) Luciferase Reporter Gene Assay

5'-N-ethylcarboxamidoadenosine (NECA), an adenosine A2b agonist, is prepared as a 10 nM solution in DMSO and then diluted to 100 μM with Assay Buffer. This solution is serially diluted in Assay Buffer to give a series of 10 NECA concentrations from 100 to 0.01 μM. 10 μl portions of the resulting NECA solutions are added to the mixtures of CHO-A2b cells and reference or test compound solutions prepared as described above (preincubated for 30 minutes), final concentrations ranging from 10 to 0.0005 μM per well. The cells are incubated at 37° C., 5% $CO_2$ and 100% humidity for 3 hours to induce release of cAMP, which then binds to cAMP binding protein (CBP) and the resulting complex interacts with the reporter plasmid to express Luciferase. 100 μl of Steady-Glo, a Luciferase assay substrate from Promega, is added to all wells to lyse the cells and generate luminescence in proportion to the amount of Lucifrease produced. The plates are left for a minimum of 5 minutes before being read on the luminescence program of a Topcount NXT microplate scintillation counter (ex Packard). Concentration—response curves are plotted from the luminescence data using Activitybase software and $K_B$ values for the antagonists under test are calculated from the shifts of the curve at a particular concentration ($K_B$=[antagonist]/(concentration ratio−1)

Compounds of the Examples hereinbelow have $K_B$ values below 300 nM in the reporter gene assay. For example, the compounds of Examples 12, 15, 16, 17, 27, 35, 36 and 38 have $K_B$ values of 31 nM, 20 nM, 24 nM, 26.5 nM, 10 nM, 4 nM, 17 nM and 12 nM respectively.

In general, compounds of formula I in free or pharmaceutically acceptable salt form also exhibit inhibition of adenosine A3 receptor activation, which may be demonstrated in the adenosine A3 receptor assay described in WO 99/64418. For instance, the compounds of Examples 7, 27, 30, 31, 34, 35 and 38 have $K_I$ values of 24 nM, 16 nM, 22 nM, 11.5 nM, 11 nM, 10 nM and 4 nM in this assay.

Having regard to their inhibition of adenosine A2b receptor activation, and, in general, their inhibition of adnosine A3 receptor activation, compounds of formula I in free or pharmaceutically acceptable salt form, hereinafter alternately referred to as agents of the invention, are useful in the treatment of conditions which are mediated by the activation of the adenosine A2b receptor or the adenosine A3 receptor, particularly inflammatory or allergic conditions. Treatment in accordance with the invention may be symptomatic or prophylactic.

Accordingly, agents of the invention are useful in the treatment of inflammatory or obstructive airways diseases, resulting, for example, in reduction of tissue damage, airways inflammation, bronchial hyperreactivity, remodelling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, excercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include acute lung injury (ALI), adult respiratory distress syndrome (ARDS), chronic obstructive pulmonary, airways or lung disease (COPD, COAD or COID), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to their anti-inflammatory activity, in particular in relation to inhibition of eosinophil activation, agents of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophiiia), bronchopuimonary aspergiliosis, poiyarterltls nodosa (including Churg-Strauss syndrome), eosinophilic granuloma and eosinophil-related disorders affecting the airways occasioned by drug-reaction.

Agents of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin.

Agents of the invention may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, and inflammatory disease in which autoimmune reactions are implicated or having an autoimmune component or aetiology, including autoimmune haematological disorders (e.g. haemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary billiary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy).

Other diseases or conditions which may be treated with agents of the invention include diabetes, e.g. diabetes mellitus type I (juvenile diabetes) and diabetes mellitus type II, diarrheal diseases, ischemia/reperfusion injuries, retinopathy, such as diabetic retinopathy or hyperbaric oxygen-induced retinopathy, and conditions characterised by elevated intraocular pressure or secretion of ocular aqueous humor, such as glaucoma.

The effectiveness of an agent of the invention in inhibiting inflammatory conditions, for example in inflammatory airways diseases, may be demonstrated in an animal model, e.g. a mouse or rat model, of airways inflammation or other inflammatory conditions, for example as described by Szarka et al, J. Immunol. Methods (1997) 202:49–57 Renzi et al, Am. Rev. Respir. Dis. (1993) 148:932–939; Tsuyuki et al., J. Clin. Invest (1995) 96:2924–2931; and Cernadas et al (1999) Am. J. Respir. Cell Mol. Biol. 20:1–8.

The agents of the invention are also useful as co-therapeutic agents for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance. Accordingly the invention includes a combination of an agent of the invention as hereinbefore described with an anti-inflammatory, bronchodilatory or antihistamine drug substance, said agent of the invention and said drug substance being in the same or different pharmaceutical composition. Such anti-inflammatory drugs include steroids, in particular glucocorticosteroids such as budesonide, beclamethasone, fluticasone, ciclesonide or mometasone, LTB4 antagonists such as those described in U.S. Pat. No. 5,451,700, LTD4 antagonists such as montelukast and zafirlukast, dopamine receptor agonists such as cabergoline, bromocriptine, ropinirole and 4-hydroxy-7-[2-[[2-[[3-(2-phenylethoxy)propyl]-sulfonyl]ethyl]-amino]ethyl]-2(3H)-benzothiazolone and pharmaceutically acceptable salts thereof (the hydrochloride being Viozan®-AstraZeneca), and PDE4 inhibitors such as Ariflo® (GlaxoSmith Kline), Roflumilast (Byk Gulden), V-11294A (Napp), BAY19-8004 (Bayer), SCH-351591 (Schering-Plough), and PD189659 (Parke-Davis). Such bronchodilatory drugs include anticholinergic or antimuscarinic agents, in particular ipratropium bromide, oxitropium bromide and tiotropium bromide, and beta-2 adrenoceptor agonists such as salbutamol, terbutaline, salmeterol and, especially, formoterol and pharmaceutically acceptable salts thereof, and compounds (in free or salt or solvate form) of formula I of PCT International Publication No. WO00/75114, which document is incorporated herein by reference, preferably compounds of the Examples thereof, especially a compound of formula

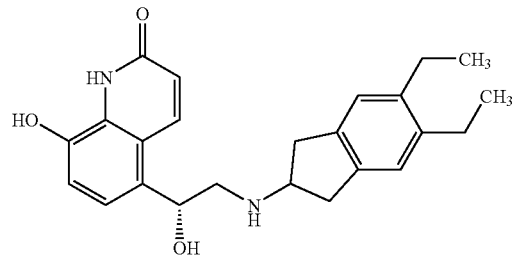

X and pharmaceutically acceptable salts thereof. Co-therapeutic antihistamine drug substances include cetirizine hydrochloride, acetaminophen, clemastine fumarate, promethazine, loratidine, desloratidine, diphenhydramine and fexofenadine hydrochloride. Combinations of agents of the invention and steroids, beta-2 agonists, PDE4 inhibitors or LTD4 antagonists may be used, for example, in the treatment of COPD or, particularly, asthma. Combinations of agents of the invention and anticholinergic or antimuscarinic agents, PDE4 inhibitors, dopamine receptor agonists or LTB4 antagonists may be used, for example, in the treatment of asthma or, particularly, COPD.

Other useful combinations of agents of the invention with anti-inflammatory drugs are those with anatagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocycohepten-8-yl]carbonyl]amino]phenyl]-methyl]tetrahydro-N,N-dimethyl-2H-pyran-4-aminium chloride (TAK-770), and CCR-5 antagonists described in U.S. Pat. No. 6,166,037 (particularly claims 18 and 19), WO00/66558 (particularly claim 8), and WO00/66559 (particularly claim 9).

In accordance with the foregoing, the invention also provides a method for the treatment of a condition mediated by activation of the adenosine A2b receptor, and/or the adenosine A3 receptor, for example an inflammatory or allergic condition, particularly an inflammatory or obstructive airways disease, which comprises administering to a subject, particularly a human subject, in need thereof a compound of formula I in free form or in the form of a pharmaceutically acceptable salt. In another aspect the invention provides a compound of formula I, in free form or in the form of a pharmaceutically acceptable salt, for use in the manufacture of a medicament for the treatment of a condition mediated by activation of the adenosine A2b receptor, and/or the adenosine A3 receptor, particularly an inflammatory or obstructive airways disease.

The agents of the invention may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

In a further aspect, the invention also provides a pharmaceutical composition comprising a compound of formula I in free form or in the form of a pharmaceutically acceptable salt, optionally together with a pharmaceutically acceptable diluent or carrier therefor. The composition may contain a co-therapeutic agent such as an anti-inflammatory, bronchodilatory or antihistamine drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

Dosages of agents of the invention employed in practising the present invention will of course vary depending, for example, on the particular condition to be treated, the effect desired and the mode of administration. In general, suitable daily dosages for oral administration are of the order of 0.1 to 10 mg/kg.

The invention is illustrated by the following Examples.

EXAMPLES 1–38

Compounds of formula I which are also of formula

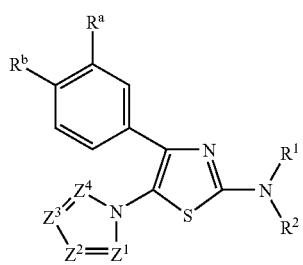

XI are shown in the following table, the method of preparation being described hereinafter. The table also shows mass spectrometry (MH+) data. The Examples are in free form, with the exception of Examples 10 and 25 which are in the form of salts with hydrobromic acid and Example 33 which is in the form of a salt with trifluoroacetic acid.

| Ex | $R^a$ | $R^b$ | $R^1$ | $R^2$ | $Z^1$ | $Z^2$ | $Z^3$ | $Z^4$ | m/s |
|---|---|---|---|---|---|---|---|---|---|
| 1 | CN | H |  | H | CH | N | CH | CH | 344 |
| 2 | CN | H | 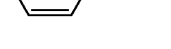 | H | N | | CH | N | CH | 243 |

-continued

| Ex | $R^a$ | $R^b$ | $R^1$ | $R^2$ | $Z^1$ | $Z^2$ | $Z^3$ | $Z^4$ | m/s |
|---|---|---|---|---|---|---|---|---|---|
| 3 | CN | H | 3-methylpyridin-yl | H | N | CH | N | CH | 345 |
| 4 | CN | H | H | (tetrahydrofuran-2-yl)carbonyl | N | CH | N | CH | 362 |
| 5 | CN | H | H | COCH$_3$ | N | CH | N | CH | 310 |
| 6 | CN | H | 4-methylpyridin-yl | H | N | CH | N | CH | 345 |
| 7 | CN | H | 2-methylpyridin-yl | H | N | CH | N | CH | 345 |
| 8 | H | Cl | 2-methylpyridin-yl | H | N | CH | N | CH | 355 |
| 9 | CN | H | H | (3-methoxyphenyl)carbonyl | N | CH | N | CH | 402 |
| 10 | CN | H | 2-methyl-5-methylpyridin-yl | H | N | CH | N | CH | 359 |
| 11 | CN | H | H | cyclopropylcarbonyl | N | CH | N | CH | 336 |
| 12 | CN | H | H | (4-methoxyphenyl)carbonyl | N | CH | N | CH | 402 |
| 13 | CN | H | 2,4-dimethyl-6-methylpyridin-yl | H | N | CH | N | CH | 373 |

-continued

| Ex | R² | Rᵇ | R¹ | R² | Z¹ | Z² | Z³ | Z⁴ | m/s |
|---|---|---|---|---|---|---|---|---|---|
| 14 | CN | H | 2-methyl-4-methylpyridin-yl (4-methyl-pyridin-2-yl with CH₃) | H | N | CH | N | CH | 359 |
| 15 | CN | H | 2,6-dimethylpyridin-yl | H | N | CH | N | CH | 359 |
| 16 | CN | H | H | 1-(5-methylthiophen-2-yl)ethanone | N | CH | N | CH | 392 |
| 17 | CN | H | 4-methylpyridin-yl | H | CH | N | CH | CH | 344 |
| 18 | CN | H | 3-methylpyridin-yl | H | N | CH | N | CH | 345 |
| 19 | CN | H | H | 1-(furan-2-yl)ethanone | N | CH | N | CH | 362 |
| 20 | H | H | pyridin-2-yl | H | N | CH | N | CH | 320 |
| 21 | H | Me | pyridin-2-yl | H | N | CH | N | CH | 334 |
| 22 | CN | H | H | 1-cyclobutylethanone | N | CH | N | CH | 350 |
| 23 | CN | H | H | 1-(pyridin-3-yl)ethanone | N | CH | N | CH | 373 |
| 24 | CN | H | 2-ethyl-6-methylpyridin-yl | H | N | CH | N | CH | 373 |
| 25 | CN | H | 4-cyanophenylmethyl | H | N | CH | N | CH | 369 |

-continued

| Ex | R² | Rᵇ | R¹ | R² | Z¹ | Z² | Z³ | Z⁴ | m/s |
|----|----|----|----|----|----|----|----|----|-----|
| 26 | CN | H | 5-(2-methoxy)pyridyl | H | N | CH | N | CH | 375 |
| 27 | CN | H | 2-pyrazinyl | H | N | CH | N | CH | 346 |
| 28 | F | H | 2-pyridyl | H | N | CH | N | CH | 338 |
| 29 | F | H | 3-pyridyl | H | N | CH | N | CH | 338 |
| 30 | F | H | 4-pyridyl | H | N | CH | N | CH | 338 |
| 31 | CN | H | 6-methoxy-2-pyridyl | H | N | CH | N | CH | 375 |
| 32 | CN | H | 6-methyl-2-pyridyl | H | CH | N | CH | CH | 358 |
| 33 | H | H | 6-methyl-2-pyridyl | H | OCH₃ | N | CH | CH | 372 |
| 34 | CN | H | 2-pyrazinyl | H | CH | N | CH | CH | 345 |
| 35 | CN | H | 2-pyrazinyl | H | OCH₃ | N | CH | CH | 360 |
| 36 | CN | H | H | 1,2-dimethyl-pyrrolyl | N | CH | N | CH | 376 |

-continued

| Ex | R² | Rᵇ | R¹ | R² | Z¹ | Z² | Z³ | Z⁴ | m/s |
|---|---|---|---|---|---|---|---|---|---|
| 37 | CN | H | (pyrazine with OCH₃) | H | N | CH | N | CH | 377 |
| 38 | CN | H | (pyrazine with OCH₂CH₂O—CH₃O substituent) | H | N | CH | N | CH | 420.9 |

PREPARATION OF SPECIFIC EXAMPLES

Example 12

N-[4-(3-Cyano-phenyl)-5-[1,2,4]triazol-1-yl-thiazol-2-yl]-4-methoxy-benzamide 4-methoxybenzoyl chloride (0.16 ml, 1.36 mmol) is added to a solution of 3-(2-amino-5-[1,2,4]triazol-1-yl-thiazol-4-yl)-benzonitrile (0.15 g, 0.56 mmol) in dry pyridine (1.5 ml). After stirring for 2 h, the reaction mixture is triturated with hot ethanol for 30 min. followed by collection of a solid by filtration. Washing the solid with ethanol and drying gives the title compound, m.s. (MH+) 402, m.p. 292–294° C.

Examples 5, 9, 11 and 22 are prepared analogously.
Starting material is prepared as follows:

3-(2-Amino-5-[1,2,4]triazol-1-yl-thiazol-4-yl)-benzonitrile

A mixture of 3-(2-bromo-2-[1,2,4]triazol-1-yl-acetyl)-benzonitrile hydrobromide (1.848 g, 5.00 mmol), thiourea (0.46 g, 1.2 mol) in ethanol is heated to 95° C. for 8 h. The solvent is removed under vacuum to give a foam which is dissolved in 3M hydrochloric acid. The product is precipitated as a white powder by the addition of concentrated aqueous ammonia to pH11. M.S. (MH+) 269.54.

Example 15

3-[2-(6-Methyl-pyridin-2-ylamino)-5-[1,2,4]triazol-1-yl-thiazol-4-yl]-benzonitrile 3-(2-Bromo-2-[1,2,4]triazol-1-yl-acetyl)-benzonitrile hydrobromide (500 mg, 1.34 mmol) is dissolved in ethanol (5 ml). (6-Methyl-pyridin-2-yl)-thiourea (208 mg, 1.34 mmol) is added and the reaction heated to 90° C. for 2 hours. The precipitate is collected and washed with ethanol twice. The solid is suspended in water and basified with concentrated ammonium hydroxide and the resulting precipitate collected and washed with water to give the title compound after drying. Mass Spec (APCI+) 360.0, m.p. 236–237° C.

The thiourea starting material is prepared as follows:

(6-Methyl-pyridin-2-yl)-thiourea

6-Methyl-pyridin-2-ylamine (1.0 g, 9.2 mmol) is dissolved in ethanol (10 ml) and benzoylisothiocyanate (1.24 ml, 9.2 mmol) is added dropwise. The mixture is heated to 40° C. with stirring for 10 minutes then allowed to cool to room temperature. The solvent is removed in vacuo and the resulting solid dissolved in 1M sodium hydroxide (15 ml) and heated under reflux for 2 hour. The resultant suspension is filtered and the solid washed copiously with water and then with cold ethanol. The solid is dried in vacuo to yield the title compound. Mass Spec (APCI+) 168.

Example 27

(3-[2-(Pyrazin-2-ylamino)-5-[1,2,4]triazol-1-yl-thiazol-4-yl]-benzonitrile)

3-([1,2,4]Triazol-1-yl-acetyl)-benzonitrile (150 mg, 0.7 mmol) is dissolved in dioxane (640 μl) and bromine (19 μl) added dropwise. The mixture is then heated at 80° C. for 6 hours. The resultant suspension is cooled to room temperature and the precipitate isolated by filtration. This precipitate, 3-(2-bromo-2-[1,2,4]triazol-1-yl-acetyl)-benzonitrile hydrobromide, (200 mg, 0.5 mmol) is dissolved in ethanol (2 ml). Pyrazin-2-yl-thiourea (0.5 mmol) is added and the reaction heated to 80° C. for 10 hours. The ethanol is removed in vacuo and the residue triturated thoroughly in 3M HCl. The resultant suspension is basified with concentrated ammonium hydroxide and the resulting precipitate filtered and washed with water then cold ethanol. The solid thus obtained is dried in vacuo to give the title compound, m.p. >250° C., m.s. (AP+) 347.

Examples 3, 6–8, 10, 13–14, 17–18, 20–21, 24–26 and 28–31 are prepared in an analogous manner from the appropriate compounds of formulae II and III.

Starting materials are prepared as follows:

3-([1,2,4]Triazol-1-yl-acetyl)-benzonitrile

3-Cyanoacetophenone (10.013 g, 69 mmol) is dissolved in dioxane (150 ml) and bromine added (3.53 ml). The mixture is stirred at room temperature for 30 minutes then the solvent is removed in vacuo and the residue taken up in acetonitrile (100 ml). Sodium triazole (7 g) is added and the mixture is stirred at room temperature overnight. The mixture is then filtered and the solid obtained discarded. The filtrate is evaporated to dryness and the solid residue taken up in 3M HCl (500 ml) with heating. The aqueous layer is decanted from a gummy residue and washed with ethyl acetate. The aqueous layer is then basified with concentrated aqueous ammonia solution and the resultant precipitate filtered and washed with water. This precipitate is dried in vacuo to give 3-([1,2,4]triazol-1-yl-acetyl)-benzonitrile, m.p. 172–173° C., m.s. (AP+) 213.

Other compounds of formula II are prepared in an analogous manner from the appropriate acetophenone.

Pyrazin-2-yl-thiourea

Aminopyrazine (2 g, 21.03 mmol) is dissolved in ethanol (20 ml) and benzoylisothiocyanate (2.82 ml) is added dropwise. The mixture is heated to 80° C. with stirring for 10 minutes then allowed to cool to room temperature. The solvent is removed in vacuo and the resulting solid dissolved in 1M sodium hydroxide (30 ml) and heated under reflux for 1 hour. The resultant suspension is filtered and the solid washed with water and a little cold methanol. The solid is dried in vacuo to yield the title compound, m.p. 239–239.5° C., m.s. (AP+) 138 ($M^+$—$NH_3$). Other thioureas of formula III are prepared in an analogous manner from the appropriate starting amine.

Example 35

(3-[5-(2-Methyl-imidazol-1-yl)-2-(pyrazin-2-ylamino)-triazol-4-yl]-benzonitrile)

3-[5-Bromo-2-(pyrazin-2-ylamino)-thiazol-4-yl]-benzonitrile (250 mg, 0.698 mmol) and 2-methylimidazole (573 mg, 6.98 mmol) are combined and heated as a melt at 150° C. for 16 h. The resulting solid is purified by flash chromatography to yield the title compound as a powder, m.p. 276–276.5° C., m.s. 360 (TOF, ES+).

Examples 1, 2 and 32–34 are prepared in an analogous manner by reaction of the appropriate compounds of formulae IV and V.

Starting materials are prepared as follows:

3-[2-(Pyrazin-2-ylamino)-thiazol-4-yl]-benzontrile 3-acetylbenzonitrile (1.0 g, 6.88 mmol) is taken up in dioxane (15 ml) and bromine (353 μl, 6.88 mmol) is added dropwise with constant stirring. The reaction is stirred for 30 minutes, then the dioxane is evaporated at reduced pressure. The resulting slurry is taken up in ethanol (15 ml) and pyrazinyl-2-thiourea (1.0 g, 6.88 mmol) is added. The reaction is then heated to 80° C. for 30 minutes, cooled to room temperature and the ethanol distilled off at reduced pressure. The solid is suspended in 3M HCl and then basified with ammonia solution. The resulting precipitate is filtered and washed with copious amounts of water and cold ethanol. Hot trituration with methanol and subsequent drying yields the title compound, m.p. 203–204° C., m.s. 280(ES+).

3-[5-Bromo-2-(pyrazin-2-ylamino)-thiazol-4-yl]-benzonitrile

3-[2-(Pyrazin-2-ylamino)-thiazol-4-yl]-benzonitrile (1.5 g, 5.36 mmol) is suspended in hot glacial acetic acid (10 ml) and bromine (0.275 ml) is added dropwise at room temperature with stirring. The resultant suspension is stirred at room temperature for 10 minutes. Water (ca. 100 ml) is added to the mixture, which is basified to pH 9 with solid potassium carbonate. The resulting precipitate is filtered and washed with water to yield 3-[S-bromo-2-(pyrazin-2-ylamino)-thiazol-4-yl]-benzonitrile, m.p. 215° C. (dec.), m.s. 279 (ES+, $M^+$—Br).

Other compounds of formula IV are prepared in an analogous manner from the appropriate compounds of formulae IX and III.

Example 36

1-Methyl-1H-pyrrole-2-carboxylic Acid [4-(3-cyano-phenyl)-5-[1,2,4]

triazol-1-yl-thiazol-2-yl]-amide

1-Methyl-1H-pyrrole-2-carbonyl chloride (110 mg) is added to a solution of 3-(2-amino-5-[1,2,4]triazol-1-yl-thiazol-4-yl)-benzonitrile (50 mg, 0.19 mmol) in dry pyridine (0.5 ml). After stirring for 16 h, water (10 ml) is added. After 3 days the precipitate is collected and washed with water. The resulting cake is triturated in refluxing ethanol for 20 min., filtered and washed with ethanol. The solid is triturated with saturated aqueous sodium bicarbonate, filtered, washed with water and dried to give the title compound. Mass Spec. (MH+) 376, m.p. 245–247° C.

Examples 4–5, 16, 19 and 23 are prepared analogously.

Example 37

3-[2-(6-Methoxy-pyrazin-2-ylamino)-5-[1,2,4]

triazol-1-yl-thiazol-4-yl]benzonitrile 3-(2-Bromo-2-[1,2,4]triazol-1-yl-acetyl)-benzonitrile hydrobromide (250 mg, 0.67 mmol) is dissolved in ethanol (2 ml). (6-Methoxy-pyrazin-2-yl)-thiourea (0.67 mmol) is added and the reaction heated to 80° C. for 10 hours. The ethanol is removed in vacuo and the residue triturated in 3M HCl. The resultant suspension is basified with concentrated ammonium hydroxide and the resulting precipitate filtered and washed with water then cold ethanol. The solid thus obtained is triturated with hot ethanol and dried in vacuo to give the title compound. Mass Spec (APCI+) 377.1.

Example 38 is prepared analogously.

The thiourea starting material is prepared as follows:

(6-Methoxy-pyrazin-2-yl)-thiourea

6-Methoxy-pyrazin-2-ylamine (0.85 g, 6.8 mmol) is dissolved in ethanol (7 ml) and benzoylisothiocyanate (0.91 ml) is added dropwise. The mixture is heated to 80° C. with stirring for 10 minutes then allowed to cool to room temperature. The solvent is removed in vacuo and the resulting solid dissolved in 1M sodium hydroxide (15 ml) and heated under reflux for 1 hour. The resultant suspension is filtered and the solid washed with water and a little cold ethanol. The solid is dried in vacuo to yield the title compound.

Example 39

(3-[5-(2-Methyl-imidazol-1-yl)-2-(pyrazin-2-ylamino)-thiazol-4-yl]

-benzontrile) methanesulfonate (3-[5-(2-Methyl-imidazol-1-yl)-2-(pyrazin-2-ylamino)-thiazol-4-yl]-benzonitrile (1 g, 2.78 mmol) is suspended in boiling pentanol (25 ml) and filtered hot to give a clear solution. Methanesulfonic acid (0.2 ml, 3.06 mmol) is added and the mixture allowed to cool to room temperature, when a solid is precipitated. Diethyl ether (25 ml) is added with stirring, and the solid is filtered off, washed with diethyl ether and then triturated with diethyl ether (25 ml). The solid obtained is filtered off, dried in vacuo and suspended in boiling acetone (20 ml). Water (2 ml), then acetone (5 ml) are added and the resulting solution allowed to cool to 4° C. The resulting solid is filtered off, washed with acetone and dried in vacuo at 80° C. over $P_2O_5$ to give the title compound, m.p. 282° C.

Starting materials are prepared as follows:

3-(2-Methylimidazol-1-yl-acetyl)-benzonitrile 3-acetylbenzonitrile (50 g, 0.345 mol) is dissolved in dioxane (600 ml) with stirring at room temperature, bromine (17.7 ml, 0.345 mol) is added in and the mixture is stirred for 30 minutes. The dioxane is removed in vacuo to give a solid which is dissolved in acetonitrile (300 ml). 2-Methylimidazole (28.3 g, 0.345 mol) is added to the solution and the mixture is stirred for 1 hour, the temperature of the mixture rising to 45° C. The precipated solid is filtered off, washed with acetonitrile, and slurried with methanol for 1 hour. After filtering to remove undissolved solid, the filtrate is evaporated in vacuo to leave a solid which is dried in vacuo at 40° C. to give the title compound, m.s. 369 (MH+).

(3-[5-(2-Methyl-imidazol-1-yl)-2-(pyrazin-2-ylamino)-thiazol-4-yl]-benzonitrile)

3-(2-Methylimidazol-1-yl-acetyl)-benzonitrile (13.8 g, 0.06 mol) is mixed with pyrazinyl-2-thiourea (9.4 g, 0.06 mol), iodine (15.6 g, 0.06 mol) and pyridine (60 ml). The mixture is stirred, initially at room temperature and then at 60° C. overnight (17.5 hours). The mixture obtained is allowed to cool to room temperature and water (50 ml) added. The solid obtained is filtered off, stirred in water (50 ml) for 30 minutes, and filtered off again. The resulting solid is dried at 40° C. in vacuo over $P_2O_5$ to give the title compound.

The invention claimed is:

1. A compound of formula

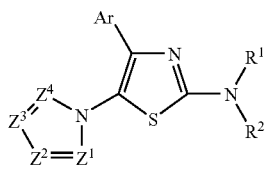

I in free or salt form, where

Ar is a $C_6$–$C_{15}$ monovalent aromatic group, $R^1$ is hydrogen, phenyl optionally substituted by one or more substituents selected from halogen, cyano, hydroxy, $C_1$–$C_8$-alkyl, $C_1$–$C_8$-haloalkyl, $C_1$–$C_8$-alkoxy, $C_1$–$C_8$-alkoxy-$C_1$–$C_8$-alkyl or acyloxy, or a 5- or 6-membered monovalent heterocyclic group, $R_2$ is hydrogen, $C_1$–$C_8$-alkyl, acyl or —$CON(R^3)R^4$, provided that $R^2$ is $C_1$–$C_8$-alkyl, acyl or —$CON(R^3)R^4$ when $R^1$ is hydrogen, $R^3$ and $R^4$ are each independently hydrogen or $C_1$–$C_8$-alkyl, or together with the nitrogen atom to which they are attached denote a 5- or 6-membered heterocyclic group, and $Z^1$, $Z^2$, $Z^3$ and $Z^4$ are each independently N or $CR^5$, at least one of them being $CR^5$, and $R^5$ is hydrogen, $C_1$–$C_8$-alkyl or $C_1$–$C_8$-alkoxy.

2. A compound according to claim 1, in which Ar is phenyl optionally substituted by one or more substituents selected from halogen, cyano, $C_1$–$C_8$-alkyl or $C_1$–$C_8$-haloalkyl.

3. A compound according to claim 1 in which Ar is phenyl optionally substituted by halogen, cyano or $C_1$–$C_8$-alkyl mete or pare to the indicated thiazole ring.

4. A compound according to claim 1, in which $R^1$ is hydrogen, phenyl optionally substituted by cyano or $C_1$–$C_4$-alkoxy, or a monovalent 6-membered N-heterocyclic group.

5. A compound according to claim 1, in which $R^2$ is hydrogen, $C_1$–$C_4$-alkylcarbonyl, $C_3$–$C_6$-cycloalkylcarbonyl, phenylcarbonyl where the phenyl group is optionally substituted by $C_1$–$C_8$-alkoxy, or heterocyclylcarbonyl in which the heterocyclyl group is 5- or 6-membered and has a ring hetero atom selected from nitrogen, oxygen and sulfer.

6. A compound according to claim 1, in which

Ar is phenyl optionally substituted by halogen or cyano, $R^1$ is hydrogen, phenyl optionally substituted by cyano or $C_1$–$C_4$-alkoxy, or a monovalent 6-membered N-heterocyclic group, $R^2$ is hydrogen, $C_1$–$C_4$-alkylcarbonyl, $C_3$–$C_6$-cycloalkylcarbonyl, phenylcarbonyl where the phenyl group is optionally substituted by $C_1$–$C_4$-alkoxy, or heterocyclylcarbonyl where the heterocyclyl group is 5- or 6-membered and has one or two ring hetero atoms selected from nitrogen, oxygen and sulfur, and either $Z^1$ and $Z^3$ each denote N and $Z^2$ and $Z^4$ each denote CH, or $Z^1$ denotes $CR^5$ where $R^5$ is hydrogen or $C_1$–$C_4$-alkyl, $Z^2$ denotes N and $Z^3$ and $Z^4$ each denote CH.

7. A compound according to claim 1, in which

Ar is phenyl substituted by halogen or cyano mete or pare to the indicated thiazole ring, $R^1$ is a monovalent 6-membered N-heterocyclic group, $R^2$ is hydrogen, and either $Z^1$ and $Z^3$ each denote N and $Z^2$ and $Z^4$ each denote CH, or $Z^1$ denotes $CR^5$ where $R^5$ is hydrogen or $C_1$–$C_4$-alkyl, $Z^2$ denotes N and $Z^3$ and $Z^4$ each denote CH.

8. A compound according to claim 1, in which

Ar is phenyl substituted by halogen or cyano mete or pare to the indicated thiazole ring, $R^1$ is hydrogen, $R^2$ is phenylcarbonyl where phenyl is optionally substituted by $C_1$–$C_4$-alkoxy, or heterocyclylcarbonyl where the heterocyclyl group is 5- or 6-membered and has a ring hetero atom selected from oxygen and sulfur, and either $Z^1$ and $Z^3$ each denote N and $Z^2$ and $Z^4$ each denote CH, or $Z^1$ denotes $CR^5$ where $R^5$ is hydrogen or $C_1$–$C_4$-alkyl, $Z^2$ denotes N and $Z^3$ and $Z^4$ each denote CH.

9. A compound of formula XI

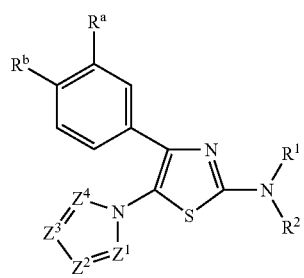

in free or salt form, where $R^a$, $R^b$, $R^1$, $R^2$, $Z^1$, $Z^2$, $Z^3$ and $Z^4$ are as shown in the following table

| $R^a$ | $R^b$ | $R^1$ | $R^2$ | $Z^1$ | $Z^2$ | $Z^3$ | $Z^4$ |
|---|---|---|---|---|---|---|---|
| CN | H | 3-methylpyridine | H | CH | N | CH | CH |
| CN | H | 6-ethyl-2-methylpyridine | H | N | CH | N | CH |
| CN | H | 3-methylpyridine | H | N | CH | N | CH |
| CN | H | H | 2-(tetrahydrofuran-2-yl)carbonyl | N | CH | N | CH |
| CN | H | H | $COCH_3$ | N | CH | N | CH |
| CN | H | 4-methylpyridine | H | N | CH | N | CH |
| CN | H | 2-methylpyridine | H | N | CH | N | CH |
| H | Cl | 2-methylpyridine | H | N | CH | N | CH |
| CN | H | H | 3-methoxybenzoyl | N | CH | N | CH |

-continued

XI

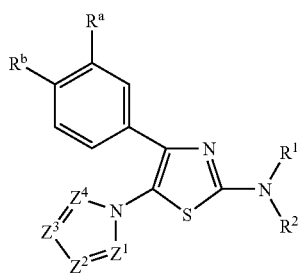

in free or salt form, where $R^a$, $R^b$, $R^1$, $R^2$, $Z^1$, $Z^2$, $Z^3$ and $Z^4$ are as shown in the following table

| $R^a$ | $R^b$ | $R^1$ | $R^2$ | $Z^1$ | $Z^2$ | $Z^3$ | $Z^4$ |
|---|---|---|---|---|---|---|---|
| CN | H | 2-methyl-5-methylpyridin-yl | H | N | CH | N | CH |
| CN | H | H | cyclopropylcarbonyl | N | CH | N | CH |
| CN | H | H | (4-methoxyphenyl)carbonyl | N | CH | N | CH |
| CN | H | 2,6-dimethyl-4-methylpyridin-yl | H | N | CH | N | CH |
| CN | H | 2-methyl-4-methylpyridin-yl | H | N | CH | N | CH |
| CN | H | 2,6-dimethylpyridin-yl | H | N | CH | N | CH |
| CN | H | H | (5-methylthiophen-2-yl)carbonyl | N | CH | N | CH |
| CN | H | pyridin-4-yl | H | CH | N | CH | CH |
| CN | H | pyridin-3-yl | H | N | CH | N | CH |

-continued
XI
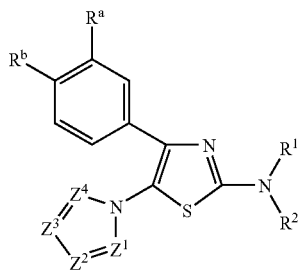
in free or salt form, where $R^a$, $R^b$, $R^1$, $R^2$, $Z^1$, $Z^2$, $Z^3$ and $Z^4$ are as shown in the following table
| $R^a$ | $R^b$ | $R^1$ | $R^2$ | $Z^1$ | $Z^2$ | $Z^3$ | $Z^4$ |
|---|---|---|---|---|---|---|---|
| CN | H | H | | N | CH | N | CH |
| H | H | | H | N | CH | N | CH |
| H | Me | | H | N | CH | N | CH |
| CN | H | H | | N | CH | N | CH |
| CN | H | H | | N | CH | N | CH |
| CN | H | | H | N | CH | N | CH |
| CN | H | | H | N | CH | N | CH |
| CN | H | | H | N | CH | N | CH |
| CN | H | | H | N | CH | N | CH |

-continued

XI

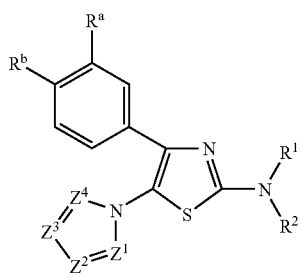

in free or salt form, where $R^a$, $R^b$, $R^1$, $R^2$, $Z^1$, $Z^2$, $Z^3$ and $Z^4$ are as shown in the following table

| $R^a$ | $R^b$ | $R^1$ | $R^2$ | $Z^1$ | $Z^2$ | $Z^3$ | $Z^4$ |
|---|---|---|---|---|---|---|---|
| F | H | 2-pyridyl | H | N | CH | N | CH |
| F | H | 3-pyridyl | H | N | CH | N | CH |
| F | H | 4-pyridyl | H | N | CH | N | CH |
| CN | H | 6-OCH₃-2-pyridyl | H | N | CH | N | CH |
| CN | H | 6-CH₃-2-pyridyl | H | CH | N | CH | CH |
| H | H | 6-CH₃-2-pyridyl | H | CCH₃ | N | CH | CH |
| CN | H | 2-pyrazinyl | H | CH | N | CH | CH |
| CN | H | 2-pyrazinyl | H | CCH₃ | N | CH | CH |
| CN | H | H | 1-methyl-2-pyrrolyl | N | CH | N | CH |

-continued

XI

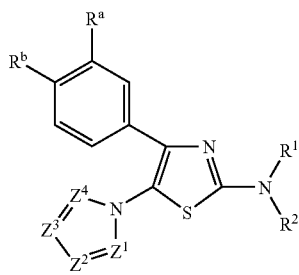

in free or salt form, where $R^a$, $R^b$, $R^1$, $R^2$, $Z^1$, $Z^2$, $Z^3$ and $Z^4$ are as shown in the following table

| $R^a$ | $R^b$ | $R^1$ | $R^2$ | $Z^1$ | $Z^2$ | $Z^3$ | $Z^4$ |
|---|---|---|---|---|---|---|---|
| CN | H | | H | N | CH | N | CH |
| CN | H | | H | N | CH | N | CH. |

10. A pharmaceutical composition comprising as active ingredient a compound according to claim 1, optionally together with a pharmaceutically acceptable diluent or carrier.

11. A method of preparing a compound of formula I in free or salt form which comprises (i) (A) for the preparation of compounds of formula I where $R^1$ is optionally substituted phenyl or a 5- or 6-membered heterocyclic group, reacting a compound of formula

II

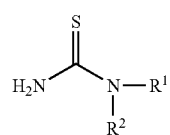

in the form of a salt, where Ar, $Z^1$, $Z^2$, $Z^3$ and $Z^4$ are as defined in claim 1 and X is halogen, with a compound of formula

III

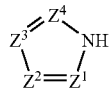

where Ret is phenyl optionally substituted by one or more substituents selected from halogen, cyano, hydroxy, $C_1$–$C_8$-alkyl, $C_1$–$C_8$-haloalkyl, $C_1$–$C_8$-alkoxy, $C_1$–$C_8$-alkoxy-$C_1$–$C_8$-alkyl and acyloxy or $R^1$ is a 5- or 6-membered monovalent heterocyclic group, and $R^2$ is H or $C_1$–$C_8$-alkyl or (B) for the preparation of compounds of Formula I where $R^1$ is optionally substituted phenyl or a 5- or 6-membered heterocyclic group, reacting a compound of formula

IV

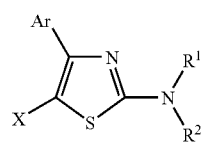

where Ar, $R^1$, $R^2$ and X are as hereinbefore defined, with a compound of formula

V

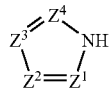

where $Z^1$, $Z^2$, $Z^3$ and $Z^4$ are as hereinbefore defined or (C) for the preparation of compounds of formula I where $R^2$ is acyl or —CON($R^3$)$R^4$, reacting a compound of formula

VI

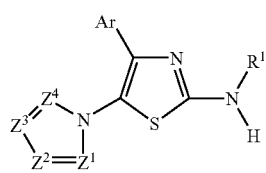

where Ar, $R^1$, $Z^1$, $Z^2$, $Z^3$ and $Z^4$ are as defined in claim 1 with, respectively, an acylating derivative of a carboxylic acid, or with a compound of formula Cl—CON($R^3$)$R^4$) where $R^3$ and $R^4$ are as defined in claim 1, and (ii) recovering the resultant compound of formula I in free or salt form.

* * * * *

UNITED STATES PATENT AND TRADEMARK OFFICE
CERTIFICATE OF CORRECTION

PATENT NO. : 7,109,202 B2  Page 1 of 1
APPLICATION NO. : 10/432302
DATED : September 19, 2006
INVENTOR(S) : Press et al.

It is certified that error appears in the above-identified patent and that said Letters Patent is hereby corrected as shown below:

Title page: Title

Item (54) should read:

-- AMINOTHIAZOLES AND THEIR USE AS ADENOSINE RECEPTOR ANTAGONISTS --.

In Column 33

The second structure should read:

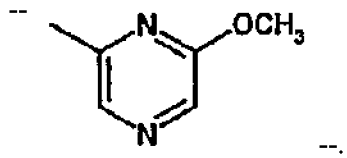

--.

Signed and Sealed this

Sixth Day of March, 2007

JON W. DUDAS
*Director of the United States Patent and Trademark Office*